United States Patent [19]

Angelchik

[11] Patent Number: 4,809,871
[45] Date of Patent: Mar. 7, 1989

[54] CLOSURE FOR SEALING AN APERTURE

[76] Inventor: Jean P. Angelchik, 1728 W. Glendale Ave., Phoenix, Ariz. 85021

[21] Appl. No.: 188,848

[22] Filed: May 2, 1988

[51] Int. Cl.⁴ ............................................. B65D 39/00
[52] U.S. Cl. .................................... 220/307; 215/355; 220/DIG. 19
[58] Field of Search ...................... 220/307, DIG. 19; 245/355, 358

[56] References Cited
U.S. PATENT DOCUMENTS 3,842,790  10/1974  Clark .................................... 215/355
4,544,074  10/1985  Evans ................................... 215/355

Primary Examiner—George T. Hall
Attorney, Agent, or Firm—William H. Drummond

[57] ABSTRACT

A device for sealing an aperture in the wall of a cavity including a tubular elastic membrane which extends from inside the cavity through the aperture to the exterior. A deformable cap closes the inner end of the tubular membrane. The membrane is radially tensioned, e.g., by an annular ring formed in the outer end of the tube to seal the membrane against the edges of the aperture.

1 Claim, 2 Drawing Sheets

CLOSURE FOR SEALING AN APERTURE

This invention relates to a closure device for sealing an aperture in the wall of a cavity.

More particularly, the invention relates to a closure device which can be implaced in sealing position rapidly and conveniently by finger pressure. In still another respect, the invention concerns such a closure device which can be quickly and conveniently removed from sealing position by finger manipulation.

Even more particularly, the invention pertains to such a closure device which is reusable. There are many instances in which it is desirable to provide a fluid-tight closure for an aperture in the wall of a cavity. Such instances range from closing the open top of a beverage bottle to closure of openings in body cavities. For example, it is frequently desirable to temporarily close a wine bottle to prevent air entering the bottle and oxidizing the wine. Alternatively, it is frequently desirable to close a carbonated beverage bottle to prevent the loss of dissolved gases which causes the beverage to "go flat."

Other examples of the need for such closures exist in the medical field. For example, it would be highly desirable to provide an effective closure for colostomy openings in the abdominal wall. Therefore, the principal object of the present invention is to provide an improved closure device for sealing an aperture in the wall of a cavity.

Yet another object of the invention is to provide such a closure device which can be easily and conveniently implaced and removed by simple finger manipulation by persons of limited skills.

Still another object of the invention is to provide such a closure device which can be implaced and removed by a person having a colostomy or ileostomy opening without the assistance of skilled attendants.

These, and other, further and more specific objects of the invention will be apparent to those skilled in the art from the following detailed description thereof taken in conjunction with the drawings in which.

Figure 1:
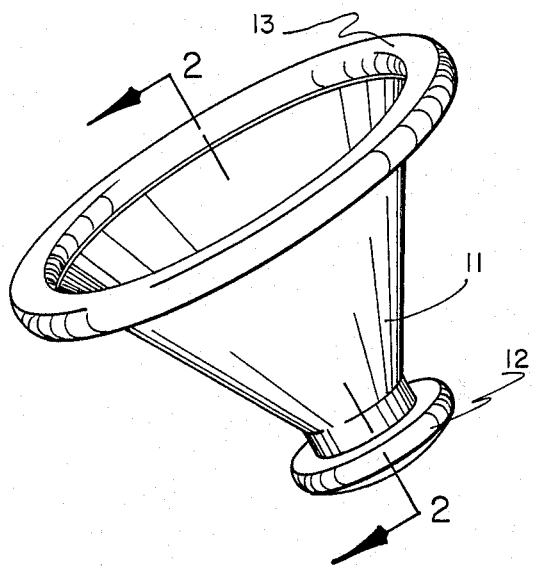
FIG. 1 is a perspecitve view of the presently preferred embodiment of the device, chosen for purposes of illustration and not by way of limitation on the scope of the invention.
Figure 2:
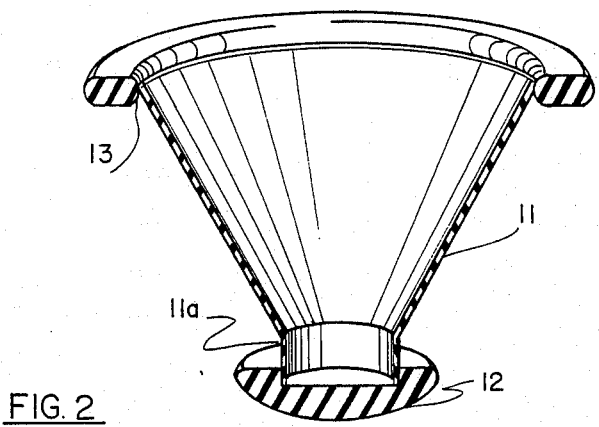
FIG. 2 is a sectional view of the device of FIG. 1 taken along section line 2—2 thereof.
Figure 3:
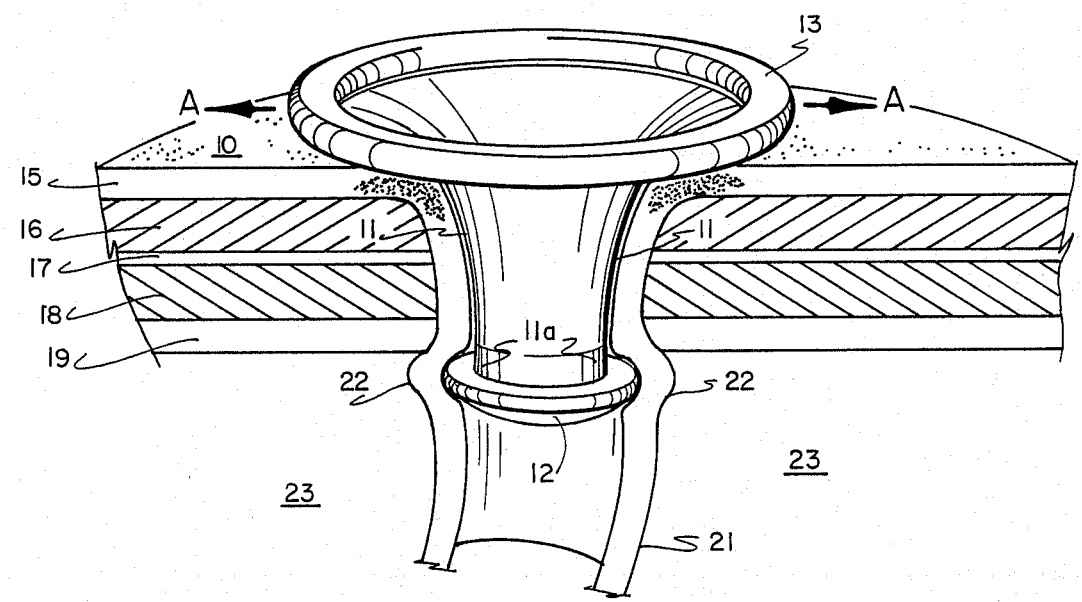
FIG. 3 is a sectional view showing the device of FIGS. 1-2 implaced in a colostomy opening in the abdominal wall of a patient to close the colostomy opening.
Figure 4:
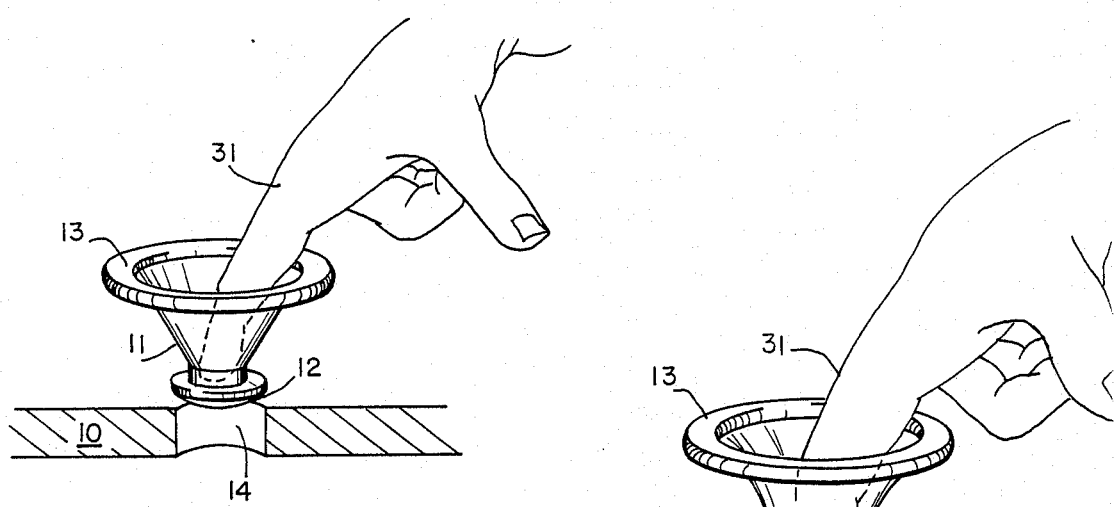
Figure 5:
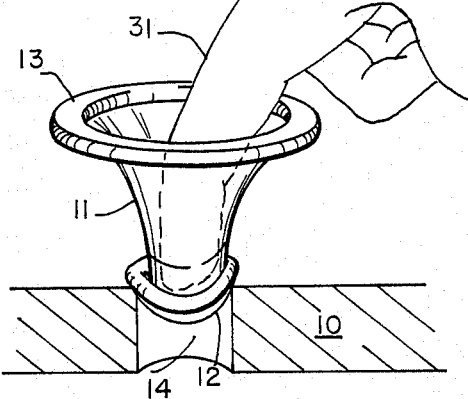
Figure 6:
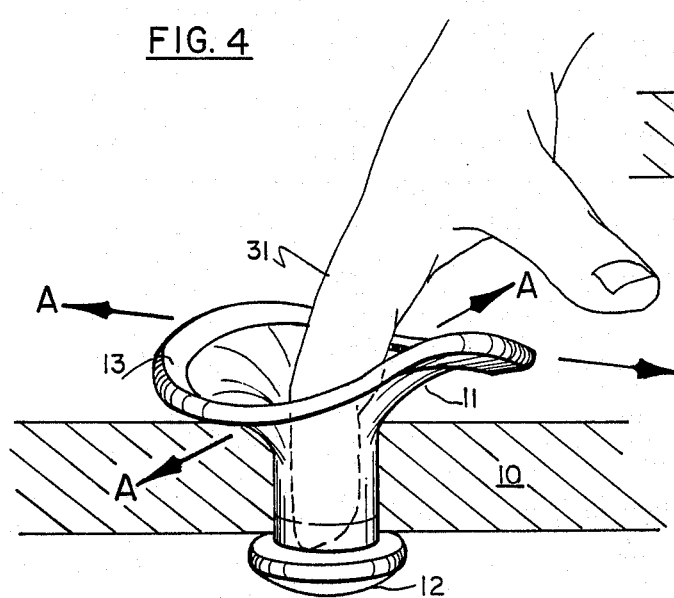
Figure 7:
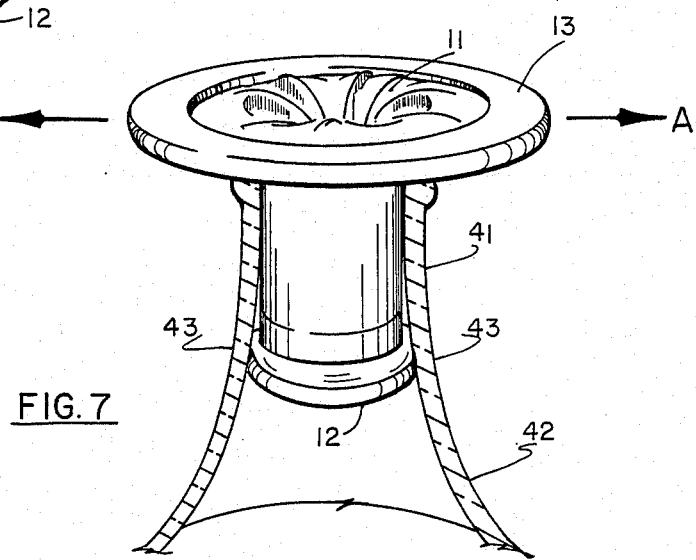

FIGS. 4, 5, and 6 illustrate the steps of implacement device to close a colostomy opening as depicted in FIG. 3; and FIG. 7 illustrates the closure of the top of a wine bottle by use of the device of FIGS. 1-2.

Briefly, in accordance with the invention, I provide a closure device for sealing an aperture in the wall of a cavity.

The device comprises a tubular elastic membrane which is dimensioned to extend from the inner and thereof within the cavity, through the aperture to the outer and thereof outside the cavity. A deformable cap closes the inner end of the tubular membrane. This cap is shaped and dimensioned to be temporarily deformed to pass through the aperture into the cavity and to autogenously reassume its undeformed shape which retains the cap within the cavity. Means are provided for radially tensioning the membrane to sealingly engage the periphery of the aperture.

Turning now to the drawings, in which like reference characters identify the same elements in the several views, FIGS. 1-2 depict the preferred embodiment of the device which consists of a hollow tubular elastic membrane 11 which can be conveniently formed of any suitable elastic material such as silicone rubber or the like. A cap member 12, fabricated of a deformable material, again, e.g., silicone rubber, is formed integrally with and closes the lower end 13 of the elastic tube 11.

An annular member 13, also preferably formed of a material such as silicone rubber is formed integrally in the upper end 14 of the elastic tubular membrane 11. The length of the tubular membrane 11, between the cap 12 and the annular member 13 can be varied to suit the thickness of the edge of the opening which is to be sealed. Generally, the length is selected so as to locate the ring 13 close to the outer surface of the wall. The diameter of the tubular membrane is not highly critical so long as radial tensioning of the membrane causes it to seal against the edges of the aperture FIG. 3 depicts a typical colostomy opening 14, formed in the abdominal wall 10. The abdominal wall consists of layers of skin 15, sub-cutaneous tissue 16, fascia 17, muscle 18, and peritoneum 19. The bowel wall and mucosa 21 are surgically attached to the periphery of an opening in the abdominal wall 10 to form the colostomy opening 14. The closure cap 12 (shown undeformed) causes slight deformation 22 of the bowel wall and mucosa 21 to retain the cap 12 within the abdominal cavity 23. The walls of the elastic tubular membrane 11 are radially tensioned by the annular ring 13 in the direction of the arrows A to cause the lower portions 11A of the tubular membrane 11 to sealingly engage the periphery of the colostomy opening 14.

FIGS. 4, 5, and 6 illustrate the steps and implacement of the device 1-2 to form a colostomy closure as shown in FIG. 3. As depicted, the device of FIGS. 1-2 is first positioned above the opening 14 with the finger 31 pressing downwardly on the deformable cap 12. The cap 12 is then deformed as shown in FIG. 5 by pressing downwardly to push it through the colostomy opening 14. Once the cap 12 is below the abdominal wall 10, it autogenously reassumes its normal shape (see FIG. 6). Upon removal of the finger 31 the annular ring 13 reassumes its normal shape by movement in the drawings of the arrows A to radially tension the elastic tubular membrane 11 and place it into sealing engagement with the periphery of the colostomy opening 14.

As shown in FIG. 7, the device of FIGS. 1-2 can, in a like manner, be inserted in the neck 4 of a wine bottle 42 such that the deformable cap 12 is retained under the tapered walls 43 of the bottle 42 and the membrane 11 is radially tensioned into sealing engagement with the neck 41 by force exerted in the direction of the arrows A by the annular ring 13.

Having described my invention in such terms as to enable those skilled in the art to understand and practice it and, having identified the presently preferred embodiments thereof, I claim:

1. A closure device for sealing an aperture in the wall of a cavity, comprising:
   (a) a tubular elastic membrane, dimensioned to extend from the inner end thereof within said cavity, through said aperture to the outer end thereof outside said cavity;

(b) deformable cap means for closing the inner end of said tubular membrane;
(c) means for radially tensioning said membrane to sealingly engage the periphery of said aperture;
said deformable cap means being shaped and dimensioned to be temporarily deformed to pass through said aperture into said cavity and to autogenously reassume an undeformed shape which retains said cap within said cavity.

* * * * *